United States Patent
Coates et al.

(10) Patent No.: US 6,462,551 B1
(45) Date of Patent: Oct. 8, 2002

(54) METHOD AND SYSTEM TO ENSURE FULL FUNCTIONALITY OF BATTERY PACK ASSEMBLY USING THERMAL IMAGING

(75) Inventors: Calvin Edward Coates, Canton; Robert John Mellchar, Dearborn, both of MI (US)

(73) Assignee: Ford Global Technologies, Inc., Dearborn, MI (US)

( * ) Notice: Subject to any disclaimer, the term of this patent is extended or adjusted under 35 U.S.C. 154(b) by 0 days.

(21) Appl. No.: 09/683,559

(22) Filed: Jan. 18, 2002

(51) Int. Cl.$^7$ ............................................. G01N 27/416
(52) U.S. Cl. ........................................ 324/431; 320/150
(58) Field of Search ................................. 324/426, 431, 324/433, 437; 320/132, 150, 153

(56) References Cited

U.S. PATENT DOCUMENTS

| | | |
|---|---|---|
| 4,361,809 A | 11/1982 | Bil et al. |
| 5,343,970 A | 9/1994 | Severinsky |
| 5,378,555 A | 1/1995 | Waters et al. |
| 5,639,571 A | 6/1997 | Waters et al. |
| 5,700,089 A | 12/1997 | McKinnon |
| 5,710,503 A | 1/1998 | Sideris et al. |
| 5,736,272 A | 4/1998 | Veenstra et al. |
| 5,886,527 A | 3/1999 | Ito |
| 6,023,637 A | 2/2000 | Liu et al. |
| 6,130,003 A | 10/2000 | Etoh et al. |
| 6,198,512 B1 | 3/2001 | Harris |
| 6,249,125 B1 | 6/2001 | Haddad et al. |
| 6,268,732 B1 | 7/2001 | Jones et al. |

Primary Examiner—Edward H. Tso
(74) Attorney, Agent, or Firm—Carlos L. Hanze

(57) ABSTRACT

The invention is a method and system to efficiently ensure functionality of a battery pack during assembly using thermal imaging. After individual battery modules are combined into sections, such as for a high voltage battery pack to power a traction motor for an electric vehicle, a power discharge test using thermal imaging is conducted on each section before combined to form the battery pack. This can determine whether any connections are loose or faulty based on the additional heat generated and detected at the site and allow them to be fixed during assembly. Further tests can include a comparison of voltage among the battery pack and each battery section and a means to adjust any battery pack that exceeds a predetermined voltage variation. The thermal image scan can obtain thermal radiation variation using infrared intensity data that can be digitized, processed, assigned color values, put on a visual display and recorded.

12 Claims, 3 Drawing Sheets

METHOD AND SYSTEM TO ENSURE FULL FUNCTIONALITY OF BATTERY PACK ASSEMBLY USING THERMAL IMAGING

BACKGROUND OF THE INVENTION

The present invention relates generally to battery pack assembly and specifically to a method to ensure full functionality of a battery pack using thermal imaging.

The need to reduce fossil fuel consumption and emissions in automobiles and other vehicles predominantly powered by internal combustion engines (ICEs) is well known. Vehicles powered by electric motors attempt to address these needs. Another alternative solution is to combine a smaller ICE with electric motors into one vehicle.

Such vehicles combine the advantages of an ICE vehicle and an electric vehicle and are typically called hybrid electric vehicles (HEVs). See generally, U.S. Pat. No. 5,343,970 to Severinsky.

The HEV is described in a variety of configurations. Many HEV patents disclose systems where an operator is required to select between electric and internal combustion operation. In other configurations, the electric motor drives one set of wheels and the ICE drives a different set.

Other, more useful, configurations have developed. For example, a series hybrid electric vehicle (SHEV) configuration is a vehicle with an engine (most typically an ICE) connected to an electric motor called a generator. The generator, in turn, provides electricity to a battery pack and another motor, called a traction motor. In the SHEV, the traction motor is the sole source of wheel torque. There is no mechanical connection between the engine and the drive wheels. A parallel hybrid electrical vehicle (PHEV) configuration has an engine (most typically an ICE) and an electric motor that work together in varying degrees to provide the necessary wheel torque to drive the vehicle. Additionally, in the PHEV configuration, the motor can be used as a generator to charge the battery pack from the power produced by the ICE.

A parallel/series hybrid electric vehicle (PSHEV) has characteristics of both PHEV and SHEV configurations and is sometimes referred to as a "powersplit" configuration. in one of several types of PSHEV configurations, the ICE is mechanically coupled to two electric motors in a planetary gear-set transaxle. A first electric motor, the generator, is connected to a sun gear. The ICE is connected to a carrier. A second electric motor, a traction motor, is connected to a ring (output) gear via additional gearing in a transaxle. Engine torque can power the generator to charge the battery pack. The generator can also contribute to the necessary wheel (output shaft) torque if the system has a one-way clutch. The traction motor is used to contribute wheel torque and to recover braking energy to charge the battery pack. In this configuration, the generator can selectively provide a reaction torque that may be used to control engine speed. in fact , the engine, generator motor and traction motor can provide a continuous variable transmission (CVT) effect. Further, the HEV presents an opportunity to better control engine idle speed over conventional vehicles by using the generator to control engine speed.

The desirability of combining an ICE with electric motors is clear. There is great potential for reducing vehicle fuel consumption and emissions with no appreciable loss of vehicle performance or driveability. The HEV allows the use of smaller engines, regenerative braking, electric boost , and even operating the vehicle with the engine shutdown. Nevertheless, new ways must be developed to optimize the HEV's potential benefits.

One such area of HEV development is ensuring full functionality of battery packs used to power the electric traction motor. The battery pack for an HEV typically produces from around 216 to 385 volts, with 6.5 amp-hours nominal capacity, and approximately 36 to 40 kW of power. Since electric powered vehicles require such high voltage and large current capacity, HEV battery packs generally combine a number of interconnected individual batteries. To ease assembly of battery pack s and to reduce battery pack cost, a standard battery size is generally used. For example, one possible battery pack could be assembled in two sections with each section having twenty individual modules. Unfortunately, during the assembly of these battery modules into battery sections, loose connections can occur resulting in high impedance on both charge and discharge as well as recording strange open circuit voltages. Unresolved, these faulty connections can cause poor vehicle performance, extended service time, warranty costs, and customer dissatisfaction.

Battery testing is certainly known in the prior art. Standard discharge rates tests on battery packs can show a severe voltage drop or unexplained voltage readings if loose or faulty connections are present. Since the source of the unexplained voltage variance is not identified during this type of test, unnecessary delays in test time result while the problem is located. Therefore, a fast and efficient method and system to ensure battery pack assembly functionality is necessary.

SUMMARY OF INVENTION

Accordingly, the present invention provides a method and system to quickly and efficiently verify full functionality of a battery pack assembly. Specifically, the present invention ensures full functionality using thermal imaging of a battery pack having at least two battery modules, the battery modules having electrode terminals combined to form a battery section. The battery modules are combined by a first set of connectors between an electrode terminal of one battery module to an electrode terminal of another battery module. A system using a first thermal image scan of the battery section during a first power discharge test determines whether the connections among the battery modules are within a first predetermined temperature tolerance. If any modules are not within the tolerance, the battery section is pulled from assembly, fixed and returned to assembly. The battery sections are combined to form a battery pack using a second set of connectors which connect a terminal of one battery section to a terminal of another battery section. Next, a system using a second thermal image scan of the battery pack during a second power discharge test determines whether the connections among the battery sections are within a second predetermined temperature tolerance and fixes them.

The present invention can also include a comparison of voltage among the battery pack and each battery section and a means to adjust any battery pack that exceeds a predetermined voltage variation.

The present invention works for battery packs wherein the battery modules are combined in either series or parallel configuration. The thermal image scan comprises a means to obtain thermal radiation variation using infrared intensity data.

The infrared intensity data can be digitized and processed so that infrared intensity values are assigned color values and put on a visual display.

Advantages of the present invention can include efficient developmental costs in that existing technologies can be used and that waste is reduced since battery sections that failed their initial testing can be fixed and reused.

Other objects of the present invention will become more apparent to persons having ordinary skill in the art to which the present invention pertains from the following description taken in conjunction with the accompanying figures.

BRIEF DESCRIPTION OF THE DRAWINGS

The foregoing objects, advantages, and features, as well as other objects and advantages, will become apparent with reference to the description and figures below, in which like numerals represent like elements and in which.

DETAILED DESCRIPTION

As the use of electric powered vehicles increases, large scale assembly of high voltage battery packs will become necessary. The present invention relates to a fast and efficient method and system to verify full functionality of a battery pack assembly. It should be noted that the present invention, though described in the context of application within a hybrid electric vehicle, could be applied to testing connections of any battery pack assembly used for any application. The present invention increases battery pack reliability by using thermal imaging techniques to detect loose or faulty battery pack module connections during power discharge tests.

Figure 1:
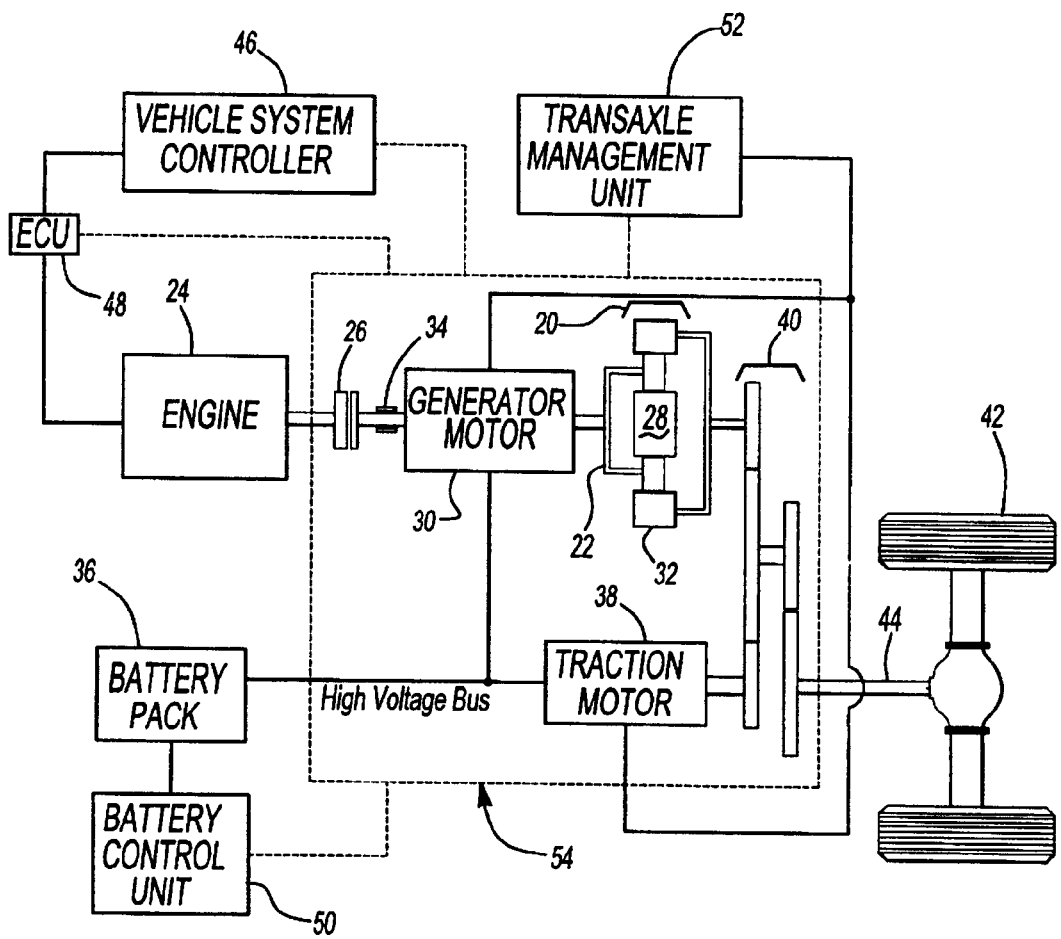
FIG. 1 illustrates a general hybrid electric vehicle (HEV) configuration.

To assist in the understanding of the present invention, FIG. 1 demonstrates just one possible configuration for an electric vehicle, specifically a parallel/series hybrid electric vehicle (powersplit) configuration.

In a basic HEV, a planetary gear set 20 mechanically couples a carrier gear 22 to an engine 24 via a one-way clutch 26. The planetary gear set 20 also mechanically couples a sun gear 28 to a generator motor 30 and a ring (output) gear 32. The generator motor 30 also mechanically links to a generator brake 34 and is electrically linked to a battery pack 36. A traction motor 38 is mechanically coupled to the ring gear 32 of the planetary gear set 20 via a second gear set 40 and is electrically linked to the battery pack 36. The ring gear 32 of the planetary gear set 20 and the traction motor 38 are mechanically coupled to drive wheels 42 via an output shaft 44.

The planetary gear set 20, splits the engine 24 output energy into a series path from the engine 24 to the generator motor 30 and a parallel path from the engine 24 To the drive wheels 42. Engine 24 speed can be controlled by varying the split to the series path while maintaining the mechanical connection through the parallel path. The traction motor 38 augments the engine 24 power to the drive wheels 42 on the parallel path through the second gear set 40. The traction motor 38 also provides the opportunity to use energy directly from the series path, essentially running off power created by the generator motor 30. This reduces losses associated with converting energy into and out of chemical energy in the battery pack 36 and allows all engine 24 energy, minus conversion losses, to reach the drive wheels 42 .

A vehicle system controller (VSC) 46 controls many components in this HEV configuration by connecting to each component's controller. An engine control unit (ECU) 48 connects to the engine 24 via a hardwire interface. All vehicle controllers can be physically combined in any combination or can stand as separate units. They are described as separate units here because they each have distinct functionality. The VSC 46 communicates with the ECU 48, as well as a battery pack control unit (BCU) 50 and a transaxle management unit (TMU) 52 through a communication network such as a controller area network (CAN) 54. The BCU 50 connects to the battery pack 36 via a hardwire interface. The TMU 52 controls the generator motor 30 and traction motor 38 via a hardwire interface.

Figure 2:
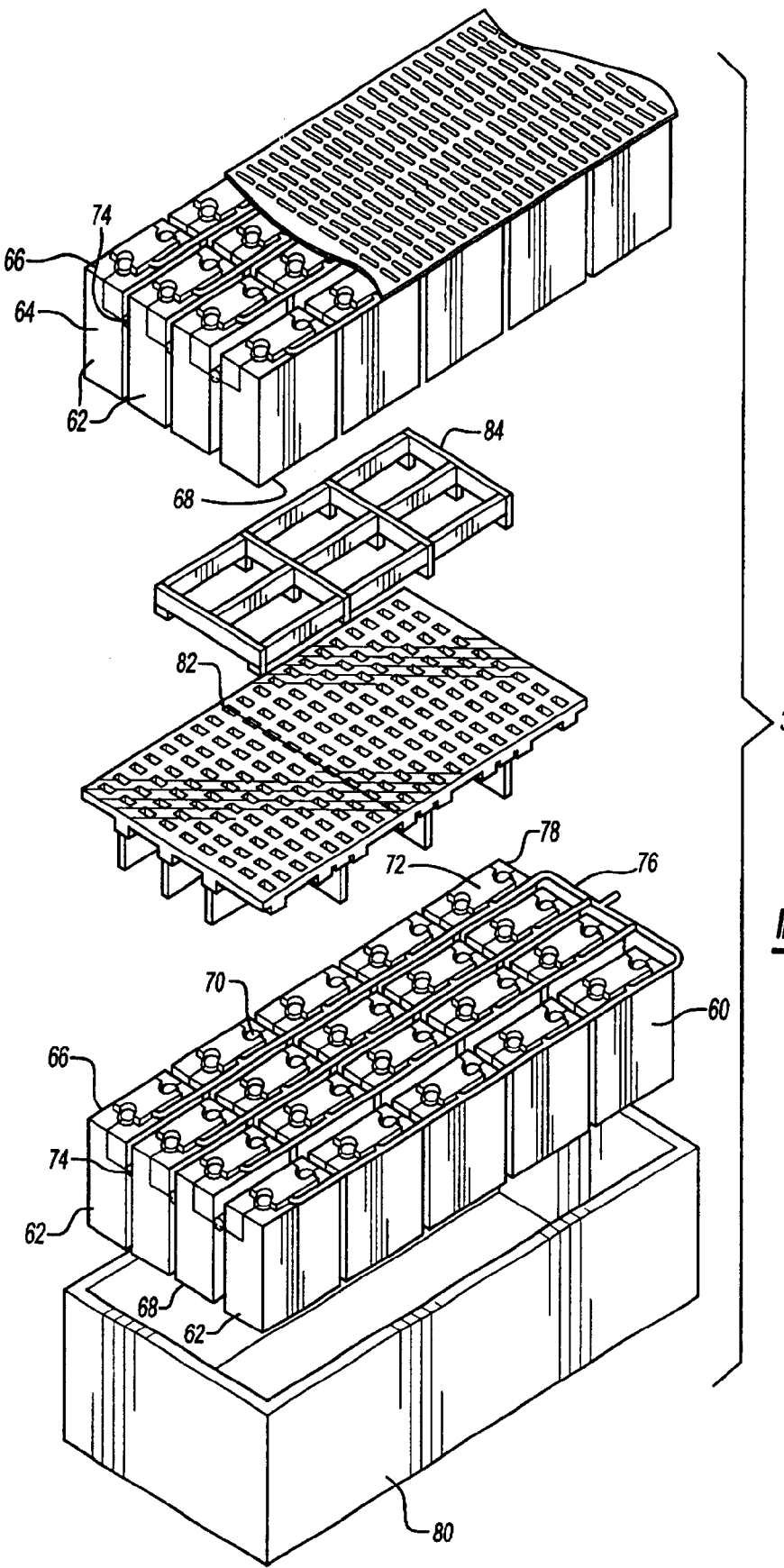
FIG. 2 illustrates an exploded view of an example of a battery pack assembly.

FIG. 2 illustrates an exploded view, partially cut away, of a battery pack 36 useful for providing the traction force for an electric vehicle such as an HEV. The battery pack 36 can have a housing 80, a tray 82 and a divider 84. The battery pack 36 can have two sections (layers or trays) of individual interconnected battery modules. A first lower section 60 in FIG. 2 has four rows of battery modules 62, each row containing five battery modules 62. Each battery module 62 is made up of a number of internal cells (not shown). A second upper section 64 of battery modules includes four rows of battery modules 62, each row having five battery modules 62. For this illustration, sections 60 and 64 are stacked one atop the other and are held in an upright orientation, though many other types of configurations are possible. Sections 60 and 64 include a top surface 66 and a bottom 68. Top surface 66 can include electrode terminals 70 and gas vents 72. The terminals 70 are generally connected in series by connectors 74 although the invention could still be used on a battery section combined in a parallel configuration. A gas conduit 76 connects each gas vent 72 and centrally vents gasses expelled from the battery modules 62. The battery top surface 66 includes a shoulder area 78 designed to carry the weight of the second upper layer 64 of battery modules 62. The shoulder area 78 generally encircles the electrode terminals 70 and the gas vents 72.During the assembly of the battery module connectors 74, some connections may be loose or faulty. Prior art testing procedures for a battery pack 36 involved standard battery power discharge rate test. Any loose or faulty connectors 74 would cause a voltage drop for the overall system, but would not identify the source of this impedance.

The present invention uses thermal imaging to identify an unexpected impedance in a battery pack 36 during its assembly. Electric impedance is essentially a type of electrical resistance that generates heat. The present invention uses thermal imaging techniques to identify loose or faulty connections during the standard battery power discharge rate tests.

Thermal imaging is known in the prior art, most notably in medical applications. Living cells within a biological body are constantly undergoing metabolic activities. These biochemical and physical metabolic processes generate heat. Certain cells, like cancer cells, have been shown to have a high metabolic rate, thus producing a high amount of heat relative to other cells. On the other hand, bones have a lower metabolic rate and generate lower amount of heat. Aging or lifeless cells do not emit heat, but rather absorb heat.

A thermal image scanning system can be configured to scan an area on a patient or a device, such as the battery pack 36, to obtain thermal radiation variation using infrared intensity data. The data can be digitized and processed prior to display. The data processing can include a function in which infrared intensity values are assigned color values in accordance with an output window. By redefining the mapping of the output window to the color spectrum, the data can be manipulated such that the visual display shows thermal variation within the scanned area.

Figure 3:
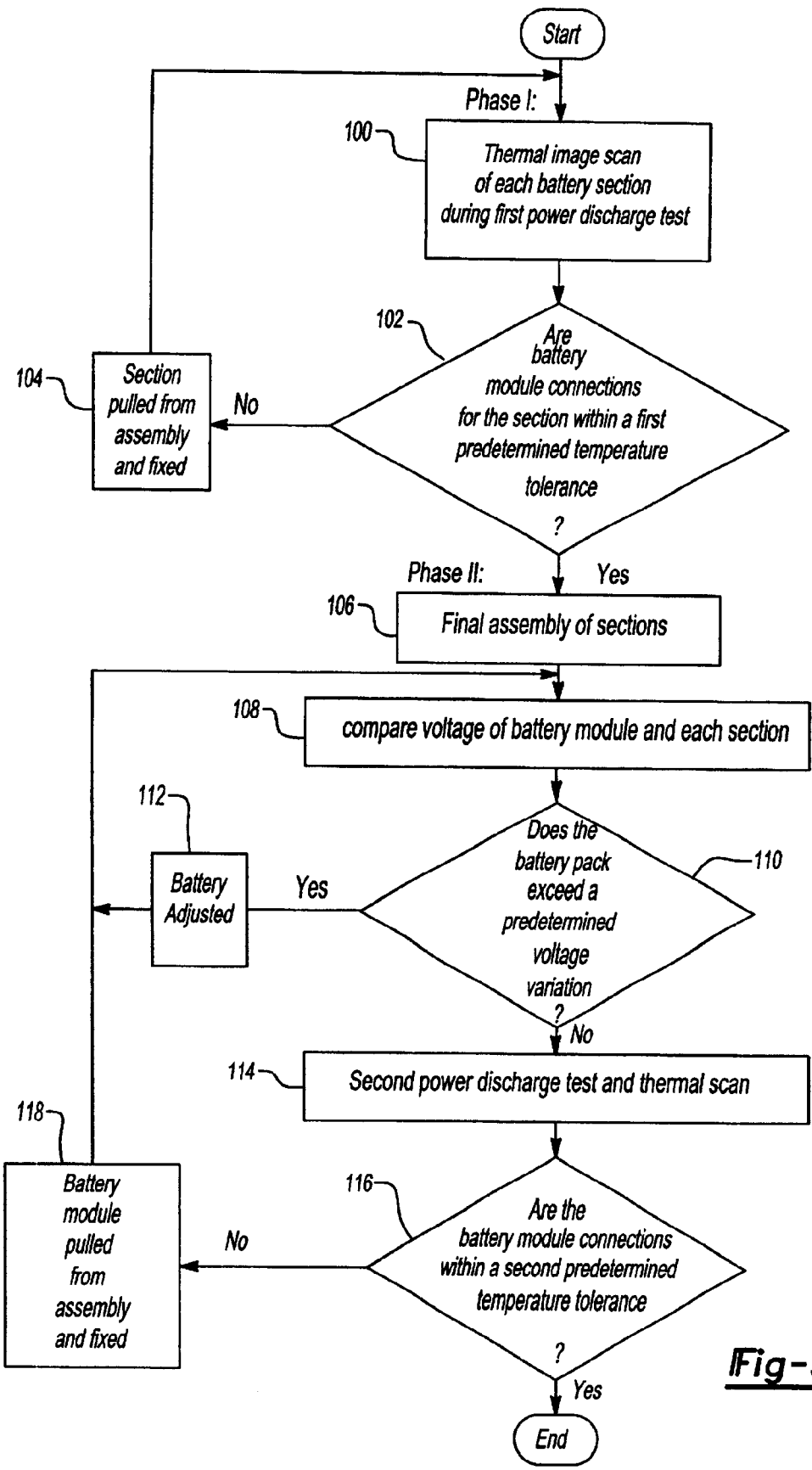
FIG. 3 illustrates a testing strategy of the present invention.

The thermal image testing for the present invention battery pack 36 assembly is accomplished in two phases. The system illustrated in FIG. 3 begins phase one at step 100 for each battery section 60 and 64 assembled using proper torquing techniques. The twenty battery modules 62 are subjected to a power discharge test. A thermal scan of the battery section is taken. The system moves to step 102 to determine if the battery module 62 connections are within a predetermined tolerance for that section. Several ways exist in the art to make this determination from software applications to manual review of the scanner readout of a visual display by an operator. For example, the system can digitize and process infrared intensity values and assigns color values that are displayed. If at step 102 the system determines some connections are not within the predetermined tolerance (i.e., the connection is generating heat above the predetermined tolerance), the system moves to step 104 where the section is pulled from assembly and fixed. From step 104, the system returns to step 100. This eliminates manufacturing waste since the failed pieces can be reused.

If at step 102, all battery module 62 connections are within the first predetermined temperature tolerance, the system can proceed to phase two at step 106 where final assembly of the battery sections occurs. The battery sections 60 and 64 are combined with connectors between terminals of each of the battery sections (not shown in FIG. 3). Step 106 is followed by step 108 and includes a comparison of individual battery section 60 and 64 voltages as well as the voltage of the overall battery pack 36. If the comparison shows the battery pack 36 needs adjustment at step 110 after a determination that a voltage exceeds a predetermined voltage variation, the system proceeds to step 112, makes the adjustments and returns to step 108. Adjustments can include tightening the connection to a predetermined torque tolerance or cleaning the terminals.

If no at step 110, the system proceeds to 114 where a second power discharge test occurs including a second thermal image scan. This second thermal image scan at step 116 determines whether the overall battery module 62 connections are within a second predetermined temperature tolerance. The thermal imaging may not detect problems at the battery modules 62 or section levels 60 and 64, but should detect problems in the connections from the battery pack 36 to any high voltage loads. If no at step 116, i.e., high voltage connection problems are detected, the system proceeds to step 118 where corrections are made. From there, the system returns to step 108. If yes at step 116, i.e., no problems are detected, the system ends.

The above-described embodiment of the invention is provided purely for of example. Many other variations, modifications, and applications of the invention may be made.

What is claimed is:

1. A system to ensure full functionality of a battery pack using thermal imaging, comprising:
    at least two battery modules, the battery modules having electrode terminals;
    a battery section comprising an electrical combination of the battery modules, the battery modules combined by a first set of connectors between an electrode terminal of one battery module to an electrode terminal of another battery module;
    a system using a first thermal image scan of the battery section during a first power discharge test to determine whether the connections among the battery modules are within a first predetermined temperature tolerance;
    a battery pack comprising an electrical combination of at least two battery sections, wherein a second set of connectors connect a terminal of one battery section to a terminal of another battery section;
    a system using a second thermal image scan of the battery pack during a second power discharge test to determine whether the connections among the battery sections are within a second predetermined temperature tolerance; and
    a means to fix any connections that exceed the first or second predetermined temperature threshold.

2. The system of claim 1 wherein the system further comprises a comparison of voltage among the battery pack and each battery section and a means to adjust any battery pack that exceeds a predetermined voltage variation.

3. The system of claim 1 wherein the battery module connections are combined in a series configuration.

4. The system of claim 1 wherein the battery module connections are combined in a parallel configuration.

5. The system of claim 1 wherein the thermal image scan comprises a means to obtain thermal radiation variation using infrared intensity data.

6. The system of claim 5 wherein infrared intensity data is digitized and processed so that infrared intensity values are assigned color values and put on a visual display.

7. A method of ensuring full functionality of a battery pack using thermal imaging during assembly, the steps comprising:
    combining at least two battery modules to form a battery section by connecting the battery modules with a first set of connectors between an electrode terminal of one battery module to an electrode terminal of another battery module;
    scanning a first thermal image of the battery section during a first power discharging test;
    determining whether the connecting among all the battery modules within the battery section are within a first predetermined temperature tolerance;
    fixing any connections not within the first predetermined temperature tolerance;
    combining the battery sections to form a battery pack, by connecting the battery sections with a second set of connectors between an electrode terminal of one battery section to an electrode terminal of another battery section;
    scanning a second thermal image of the battery pack during a second power discharging test;
    determining whether the connecting among all the battery sections within the battery pack are within a second predetermined temperature tolerance; and
    fixing any connections not within the second predetermined temperature tolerance.

8. The method of claim 7 wherein the system further comprises the step of comparing voltage output among the battery pack and each battery section and adjusting any battery pack that exceeds a predetermined voltage variation.

9. The method of claim 7 wherein the step of combining the battery modules occurs in a series configuration.

10. The method of claim 7 wherein the step of combining the battery modules occurs in a parallel configuration.

11. The method of claim 7 wherein scanning the first and second thermal image comprises the step of obtaining thermal radiation variation using infrared intensity data.

12. The method of claim 11 wherein the step of obtaining thermal radiation variation comprises the steps of digitizing and processing infrared intensity data, assigning color values to infrared intensity values, and displaying the colors visually.

\* \* \* \* \*